US010478417B2

(12) United States Patent
Fong et al.

(10) Patent No.: US 10,478,417 B2
(45) Date of Patent: Nov. 19, 2019

(54) FORMULATION FOR EFFECTIVE TOCOTRIENOL DELIVERY

(71) Applicant: KL-KEPONG OLEOMAS SDN BHD, Petaling Jaya, Selangor (MY)

(72) Inventors: Chee Wai Fong, Singapore (SG); Yee Wei Ung, Pelabuhan Klang (MY); Jordan Todorov Petkov, Cheshire (GB)

(73) Assignee: KL-KEPONG OLEOMAS SDN BHD, Petaling Jaya, Selangor (MY)

( * ) Notice: Subject to any disclaimer, the term of this patent is extended or adjusted under 35 U.S.C. 154(b) by 0 days.

(21) Appl. No.: 16/205,433

(22) Filed: Nov. 30, 2018

(65) Prior Publication Data
US 2019/0111021 A1 Apr. 18, 2019

Related U.S. Application Data

(62) Division of application No. 15/529,197, filed as application No. PCT/MY2015/050143 on Nov. 19, 2015.

(30) Foreign Application Priority Data

Nov. 25, 2014 (MY) .............................. PI2014703502

(51) Int. Cl.
A61K 31/355 (2006.01)
A61K 9/107 (2006.01)
A61K 47/26 (2006.01)
A61K 47/14 (2017.01)
A61K 47/12 (2006.01)
A61K 9/48 (2006.01)
A61K 9/00 (2006.01)
A23L 33/15 (2016.01)
A61K 47/44 (2017.01)

(52) U.S. Cl.
CPC ............ A61K 31/355 (2013.01); A23L 33/15 (2016.08); A61K 9/0053 (2013.01); A61K 9/107 (2013.01); A61K 9/4825 (2013.01); A61K 9/4841 (2013.01); A61K 47/12 (2013.01); A61K 47/14 (2013.01); A61K 47/26 (2013.01); A61K 47/44 (2013.01); A23V 2002/00 (2013.01)

(58) Field of Classification Search
None
See application file for complete search history.

(56) References Cited

U.S. PATENT DOCUMENTS 6,596,306 B1 * 7/2003 Ho ...................... A61K 9/1075
424/450
6,667,048 B1 * 12/2003 Lambert .............. A61K 9/0019
424/405

2004/0110842 A1 * 6/2004 Liang .................. A61K 9/1075
514/571
2006/0188534 A1 8/2006 Muller
2014/0025370 A1 1/2014 Bonnet et al.

FOREIGN PATENT DOCUMENTS

| CN | 1107298 | 8/1995 | |
|---|---|---|---|
| GB | 1 300 516 | 12/1972 | |
| JP | 2003-292489 | 10/2003 | |
| JP | 2013-60551 | 4/2013 | |
| JP | 2014-528150 | 10/2014 | |
| WO | WO-2012033478 A1 * | 3/2012 | ........... A61K 9/1075 |
| WO | WO 2013/059729 | 4/2013 | |

OTHER PUBLICATIONS

Glyceryl Trioleate (Sigma-Aldrich Online Catalog, Glyceryl trioleate; accessed at https://www.sigmaaldrich.com/catalog/product/sigma/t7140?lang=en&region=US, on Feb. 3, 2019; hereinafter "Glyceryl Trioleate"). (Year: 2019).*
International Search Report issued in PCT/MY2015/050143 dated Feb. 15, 2016.
Written Opinion of the International Searching Authority issued in PCT/MY2015/050143 dated Feb. 15, 2016.
International Preliminary Report on Patentability issued in PCT/MY2015/050143 dated Oct. 28, 2016.
Alqahtani et al., "Nonlinear Absorption Kinetics of Self-Emulsifying Drug Delivery Systems (SEDDS) Containing Tocotrienols as Lipophilic Molecules: In Vivo and In Vitro Studies," The AAPS Journal, vol. 15, No. 3: 684-695 (Jul. 2013).
Alqahtani et al., "Enhanced Solubility and Oral Bioavailability of γ-Tocotrienol Using a Self-Emulsifying Drug Delivery System (SEDDS)," Lipids, vol. 49, issue 8: 819-829 (Aug. 2014).
Yap et al., "Influence of lipolysis and droplet size on tocotrienol absorption from self-emulsifying formulations," International Journal of Pharmaceutics, vol. 281: 67-78 (2004).
Julianto et al.. "Improved bioavailability of vitamin E with a self emulsifying formulation" International Journal o Pharmaceutics, vol. 200: 53-57 2000 XP-001030779.
Office Action issued in AU Appln. No. 2015354848 dated Jan. 24, 2018.
Office Action issued in NZ Appln. No. 731986 dated Oct. 20, 2017.
Office Action issued in NZ Appln. No. 731986 dated May 29, 2018.
Notice of Acceptance issued in AU Appln. No. 2015354848 dated Sep. 4, 2018.
Notice of Acceptance issued in NZ Appln. No. 731986 dated Aug. 16, 2018.
Search Report issued in EP Appln. No. 15863611.8 dated Jun. 22, 2018.
Office Action issued in IN Appln. No. 201717017689 dated Jul. 4, 2019.
Office Action issued in JP Appln. No. 2017-545845 dated Sep. 3, 2019 (w/ translation).
Office Action issued in MY Appln. No. PI 2014703502 dated Mar. 15, 2019.
Office Action issued in PH Appln. No. 1/2017/500943 dated Jul. 2, 2019.

* cited by examiner

Primary Examiner — Bethany P Barham
Assistant Examiner — Dominic Lazaro
(74) Attorney, Agent, or Firm — Nixon & Vanderhye P.C.

(57) ABSTRACT

The present invention disclosed a formulation in the form of self-emulsifying drug delivery formulation for improved delivery of tocotrienols comprising a fat-soluble compound, at least one emulsifier, and an oil carrier. The formulation shows an improved bioavailability of tocotrienols.

13 Claims, 4 Drawing Sheets

FORMULATION FOR EFFECTIVE TOCOTRIENOL DELIVERY

This application is a divisional of U.S. application Ser. No. 15/529,197 filed May 24, 2017, which is the U.S. national phase of International Application No. PCT/MY2015/050143 filed Nov. 19, 2015, which designated the U.S. and claims priority to MY Patent Application No. PI 2014703502 filed Nov. 25, 2014, the entire contents of each of which are hereby incorporated by reference.

FIELD OF INVENTION

The present invention relates generally to a formulation for fat-soluble substances. More particularly, the invention relates to a self-emulsifying drug delivery formulation for improved delivery of tocotrienol isomers.

BACKGROUND OF THE INVENTION

Vitamin E is a collective name for a family of eight related fat-soluble compounds commonly found in vegetation and seeds with distinctive antioxidant activities, namely the four isomers of tocopherols and four isomers of tocotrienols. The tocopherol and tocotrienol subfamilies are each composed of alpha, beta, gamma and delta that have varying levels of biological activity. Research studies indicate that antioxidants protect cells from the damaging effects of free radicals, which are molecules containing an unpaired electron, and are known to contribute to the development of cancer and cardiovascular disease.

Therefore, vitamin E emerged as an essential fat-soluble nutrient that functions as an antioxidant in the human body to prevent disease and to promote health. Previously, the alpha-tocopherol has been considered to be the most active form. However, recent years of scientific research clearly show that tocotrienols are different from the commonly used vitamin E form i.e. alpha-tocopherol and confer properties that are stronger and often unique from tocopherols. Tocotrienols are distributed throughout the human body via the bloodstream, with particular accumulations found in various body tissues including the brain, heart, skin, cardiac muscle, liver, and adipose tissue after oral dosing. Therefore, recent developments suggest that the tocotrienol subfamily of natural vitamin E is better antioxidant than tocopherol subfamily as having powerful neuroprotective, tumor suppressive effect and cholesterol lowering properties.

The human body absorbs fat and oil in the gastrointestinal system by solubilising them into micelles through the secretion of bile salts and acids, followed by digestion by lipases. There is high inter-individual variability in this absorption process resulting in varying doses between different persons. In addition, the secretion of bile salts and acids is dependent and stimulated by a fatty diet, which can vary greatly between the different meals consumed. Like all fat-soluble nutrients and dietary lipids, the oral absorption of tocotrienols is low, highly variable and dependent upon formulation parameters. To circumvent such variables and to achieve consistent high amount of absorption of fat-based vitamins and drugs including vitamin E tocotrienols, a self-emulsifying drug delivery system (SEDDS) has been developed using different types of surfactants and oil carriers. Existing SEDDS invention for palm-derived vitamin E rich in tocotrienols is able to deliver predominantly the alpha-tocopherol isomer of Vitamin E. Moreover, this delivery is at the expense of tocotrienols isomers, whose antioxidant activity might reach from 40 to 60 times that of tocopherols.

Therefore the need exists for providing a self-emulsifying delivery system with effective formulation that preferentially increases the oral bioavailability of tocotrienol isomers over alpha-tocopherol.

The self-emulsifying formulation of the present invention provides a useful dosage form with consistent and enhanced levels of tocotrienol isomers being absorbed in-vivo upon oral ingestion which is independent of dietary fats.

SUMMARY OF INVENTION

The present invention discloses a formulation in the form of self-emulsifying drug delivery formulation which shows enhanced bioavailability of tocotrienol isomers upon oral ingestion. The formulation of the present invention comprises of fat soluble compound, an effective amount of emulsifier combination and an oil carrier.

The above and other aspects, advantages, and novel features of the invention will become apparent from the following detailed description of the invention.

DETAILED DESCRIPTION OF THE PREFERRED EMBODIMENTS

Figure 1:
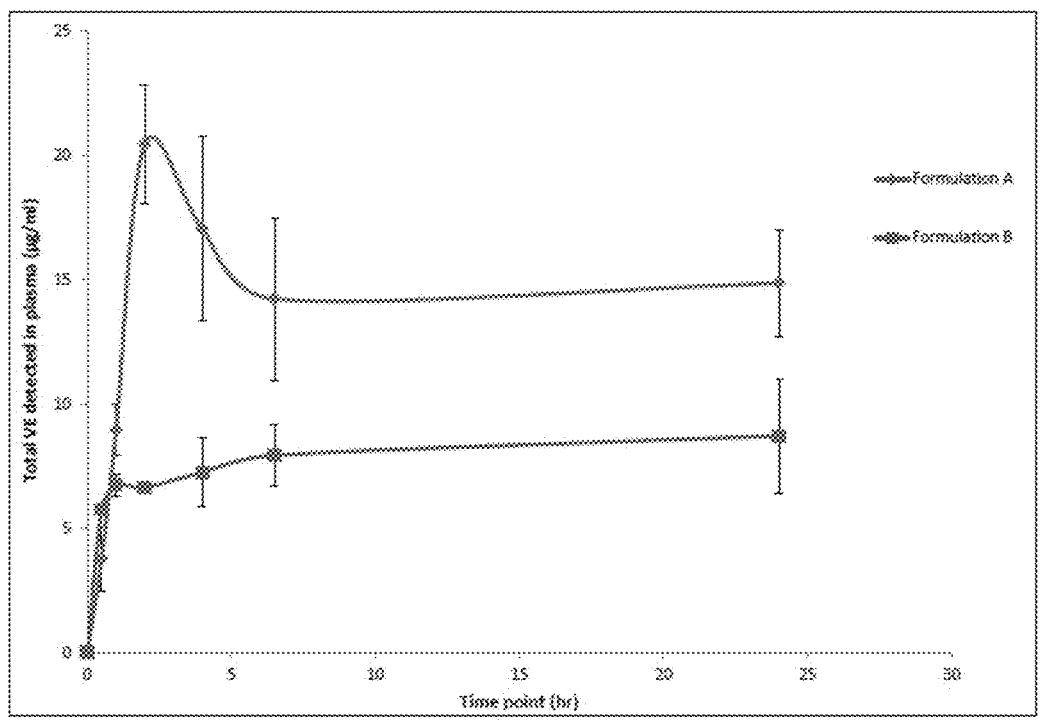
FIG. 1 shows the blood plasma concentration versus time profiles obtained after oral administration of the self-emulsifying formulations A and B with different emulsifiers.

The present invention describes a formulation of self-emulsifying drug delivery system (SEDDS) for fat-soluble drugs with an enhanced oral bioavailability and consistent high amount of absorption of tocotrienols. The formulation spontaneously forms an emulsion when contacted with an aqueous environment or in vivo administration.

Self-emulsifying drug delivery systems (SEDDS) are mixtures of oil and surfactants and have been widely used for fat-based formulation including vitamin E tocotrienols. SEDDS will form oil-in-water emulsions upon exposure to gastrointestinal fluids with mild agitation such as movement of stomach or small intestine. Thus, SEDDS could efficiently provide improvement in absorption and oral bioavailability. The selection of the right combination of oil carriers and emulsifiers to achieve consistently high level of vitamin E tocotrienols is an important and critical requisite for formulation of SEDDS as the solubility and efficiency of oral absorption of the fat-based vitamins and drugs compound from the SEDDS are determined in various oils and emulsifiers as well as the emulsifiers ratio.

The emulsifiers and oil carriers are useful excipients for providing a self-emulsifying formulation. The solubility of the poorly soluble drugs in a lipid system can be greatly increased by mixing the vitamin E with an acceptable oil carrier, and the mixture of vitamin E and oil carrier can be readily emulsified with emulsifier such as nonionic surfactants. The nonionic surfactant(s) is/are necessary for the immediate formation of oil-in-water droplets in the aqueous environment and providing a self-emulsifying process.

Surfactants include a hydrophobic component (oil soluble) and a hydrophilic component (water soluble) and are characterized by their hydrophilic-lipophilic balance (HLB). They reduce the interfacial tension between oil and water by adsorbing at the interface between oil and water, in the case where water is mixed with oil. The surfactant is capable of forming a stable emulsion when it is brought into contact with aqueous fluid.

A variety of pharmaceutically acceptable surfactants are suitable for use in the present invention. Generally, surfactants suitable for the invention are nonionic surfactants, for example, polyoxylated castor oil under the trade name, Cremophor, polyoxylated glycerides of fatty acid, polyoxyethylene sorbitan fatty acid esters, sorbitan fatty acid esters, sucrose fatty acid esters, lecithin, saponins, and the like, or mixtures thereof. Polyoxyethylene sorbitan fatty acid esters can include polysorbates, for example, polysorbate 20, polysorbate 40, polysorbate 60, and polysorbate 80. The sorbitan fatty acid esters or sorbitan esters can include sorbitan monolaurate (Span 20), sorbitan monopalmitate (Span 40), sorbitan monostearate (Span 60), and sorbitan monooleate (Span 80).

The lecithin used herein consisting of phosphoric acid, choline, fatty acids, glycerol, glycolipids, triglycerides, and phospholipids, for example, phosphatidylcholine, phosphatidylethanolamine, and phosphatidylinositol. The sucrose fatty acid esters used herein consisting of sucrose as hydrophilic group and fatty acid as lipophilic group, and generally called sugar ester. As sucrose has a total of 8 hydroxyl groups, compounds ranging from sucrose mono to octa fatty acid esters can be produced. Saponins are a class of chemical compounds found in particular abundance in various plant species. More specifically, they are amphipathicglycosides grouped phenomenologically by the soap-like foaming they produce when shaken in aqueous solutions, and structurally by having one or more hydrophilic glycoside moieties combined with a lipophilic triterpene derivative.

Fatty acid prevents phase separation between the compositions of the formulation. Examples of suitable fatty acids include, but are not limited to, oleic acid, palmitic acid, stearic acid, and the like, or mixtures thereof. The addition of a fatty acid improves the solubility of the formulation.

In a preferred embodiment, the formulation can be achieved by combining the fat-soluble compound of vitamin E rich with tocotrienols, emulsifiers and oil carrier to obtain an improved formulation.

Tests were carried out to compare bioavailability of vitamin E after oral administration of the self-emulsifying formulations with different emulsifiers and oil carriers. Formulation A, B, C, D and E, shown below, are described in Table 1, which summarizes the composition of each formulation tested.

TABLE 1

| Formulation | A | B | C | D | E |
|---|---|---|---|---|---|
| Vitamin E Emulsifiers | 20% Span-20 & Tween 80 | 20% None | 20% Span-20 & Tween 80 | 20% Span-20 & Tween 80 | 20% Labrasol & Tween 80 |
| Oil Carriers | GTO | GTO | Olive Oil | Soybean Oil | Palm Olein or Soybean Oil |
| Patent Number | NA | NA | NA | — | U.S. Pat. No. 6,596,306 |

The Formulation A of the present invention typically comprises about 5% to 60% by weight of vitamin E, about 10% to 60% by weight of emulsifier and about 0% to 70% by weight of an oil carrier. In a preferred embodiment, the Formulation A comprises about 10% to about 50% by weight of vitamin E, about 15% to about 45% by weight of emulsifier combination of sorbitan monolaurate (Span 20) and Polyoxyethylene sorbitan 20 monooleate or Polysorbate 80 (Tween 80) and about 6% to about 56% by weight of oil carrier of glycerides which is the glycerol trioleate (GTO) oil. The level of triolein (OOO, C18:1) of the main triglycerides (TG) in GTO oil is remarkably high with a content of approximately 55% to about 99% by weight of the GTO oil. In a preferred embodiment, the GTO oil contains triolein (OOO, C18:1) at about 65% to 85% by weight of the GTO oil. Similarly, the ratio of Span-20 to Tween 80 is variable and generally comprises about 1:1 to about 1:20. The preferred optimal ratio of Span-20 to Tween 80 of the Formulation A is about 1:2 to about 1:8.

Table 2 shows the breakdown of vitamin E (VE) isomers of various formulations in percentage w/w. Essentially, the profiles of the vitamin E are similar between the various formulations. The designations A and E in Table 2 denote the formulations as described above in Table 1.

TABLE 2

| Formulation | α-TP (%) | α-T3 (%) | γ-T3 (%) | δ-T3 (%) | Total VE (%) |
|---|---|---|---|---|---|
| A | 5.4 | 4.5 | 6.9 | 3.2 | 20 |
| E | 4.7 | 5.3 | 6.5 | 3.5 | 20 |

A group of rats were administered orally with Formulation A and another group of rats were administered with Formulation B at 300 mg vitamin E per kg rat body weight. The difference between the formulations is the emulsifier's blend present in Formulation A but not in Formulation B. Blood samples were withdrawn from the rats at 0.5 hr, 1 hr, 2 hr, 4 hr, 6.5 hr and 24 hr, post-administration. Plasma was extracted from blood samples and analysed. The total VE detected in blood plasma versus time profiles of Formulations A and B is shown in FIG. 1. The data shows that the total VE detected in the plasma from blood samples of the group of rats administered with formulation A with the emulsifier combination of Span-20 and Tween 80 was significantly higher than the Formulation B and is maintained for a longer time thus providing consistent high amount of absorption of vitamin E. The Area Under the Curve (AUC) of Formulation A is about 1.8 times that of Formulation B.

Figure 2:
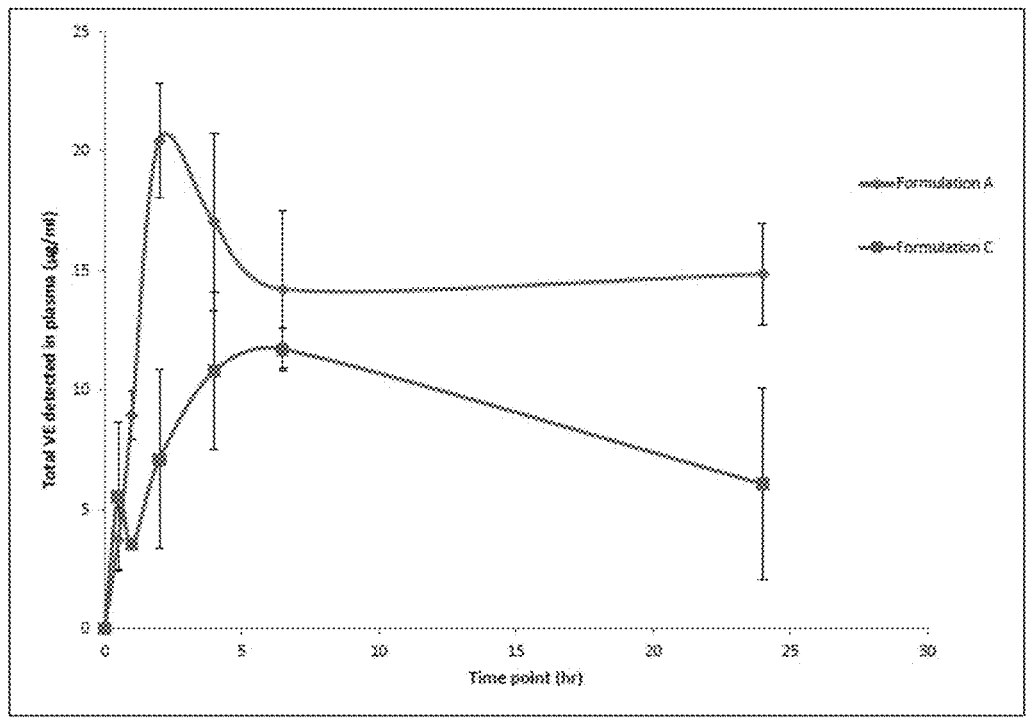
FIG. 2 illustrates the blood plasma concentration versus time profiles obtained after oral administration of the self-emulsifying formulations of A and C with different oil carriers.
Figure 3:
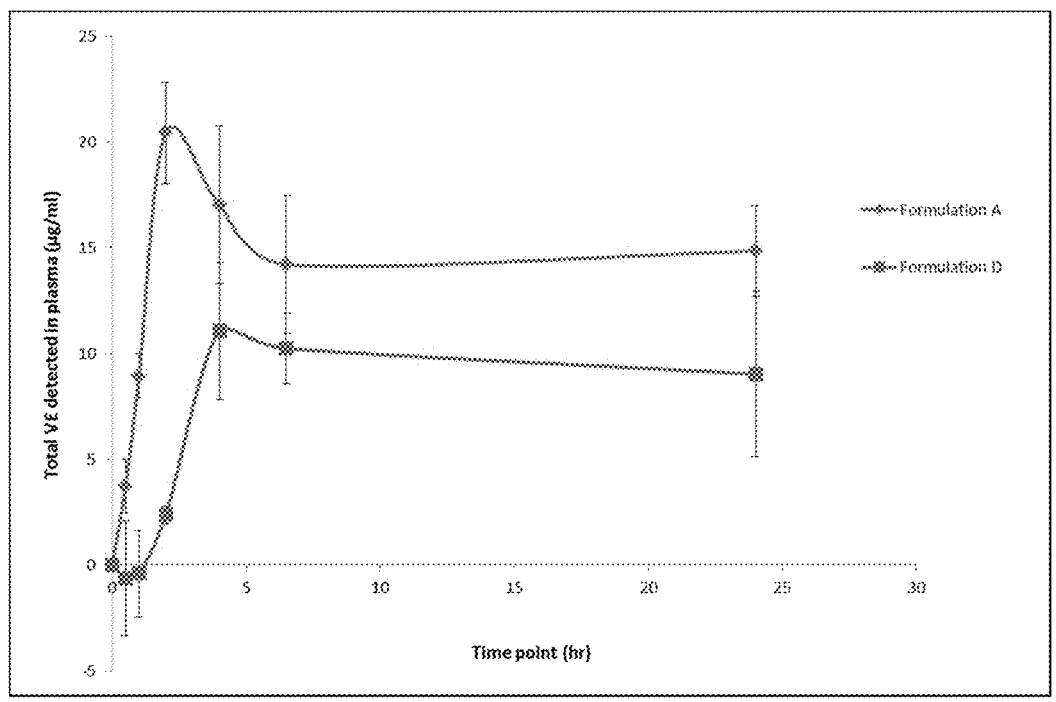
FIG. 3 shows the blood plasma concentration versus time profiles obtained after oral administration of the self-emulsifying formulations of A and D with different oil carriers.
Figure 4A:
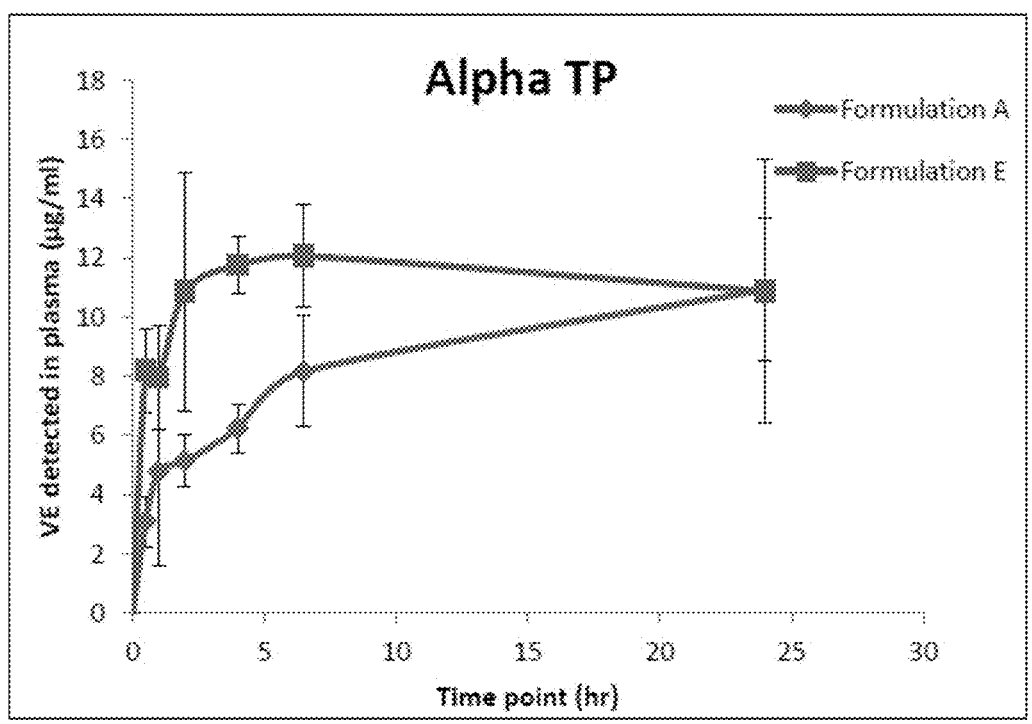
FIGS. 4a to 4d are the graphs showing the oral bioavailability of various vitamin E (VE) isomers of the Formulation A and E.
Figure 4B:
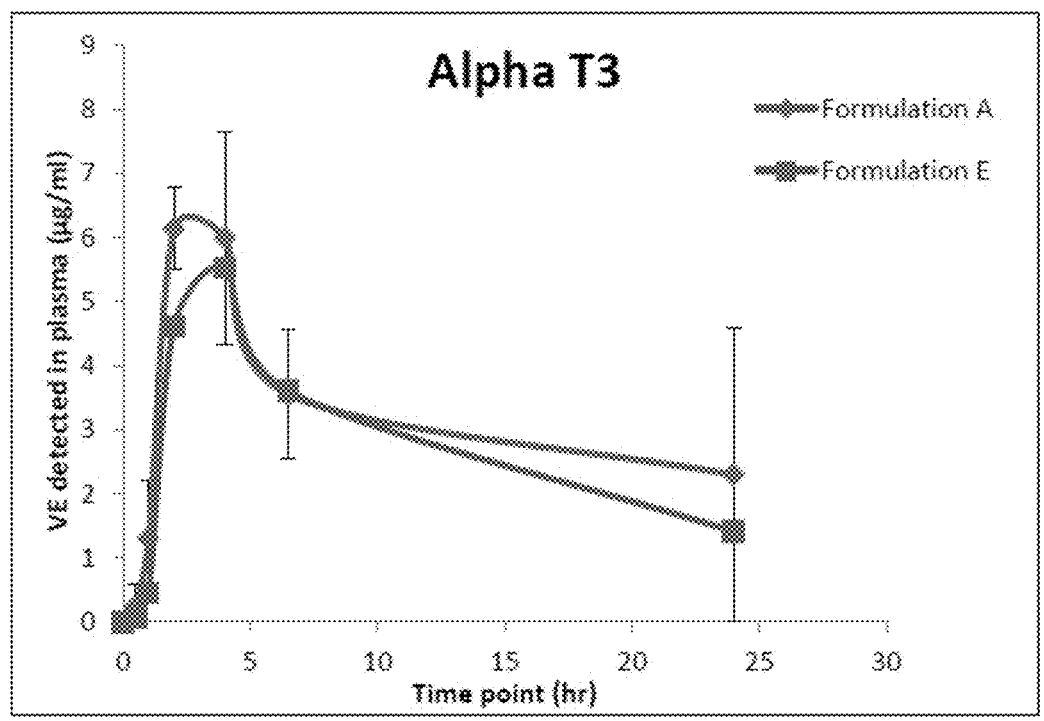
Figure 4C:
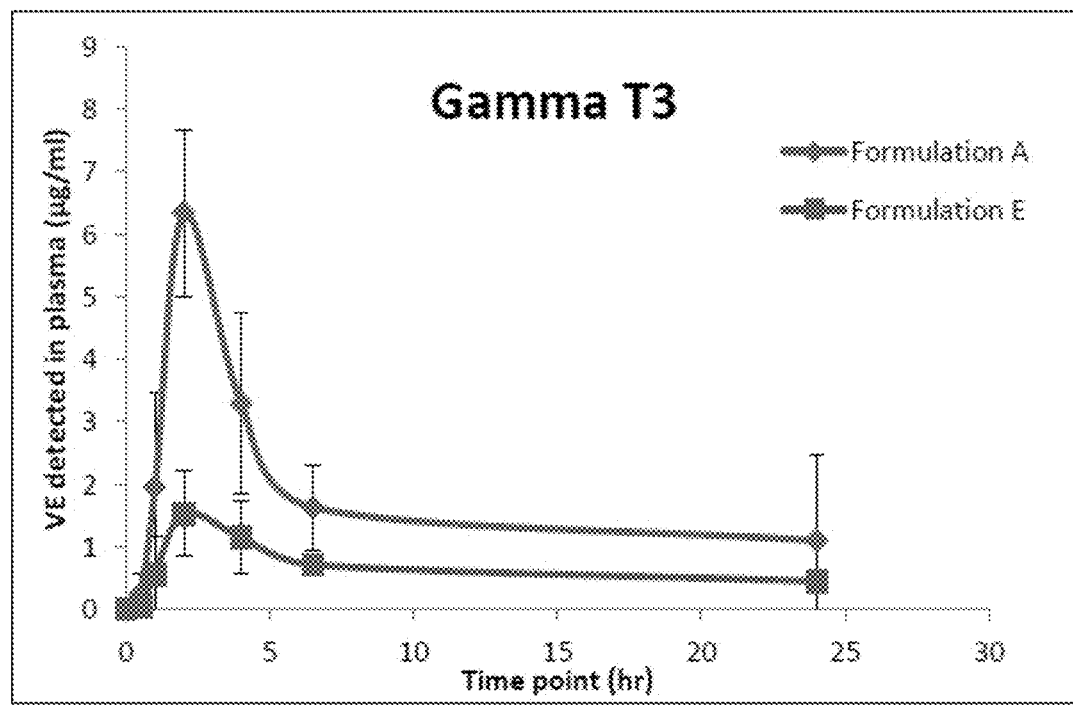
Figure 4D:
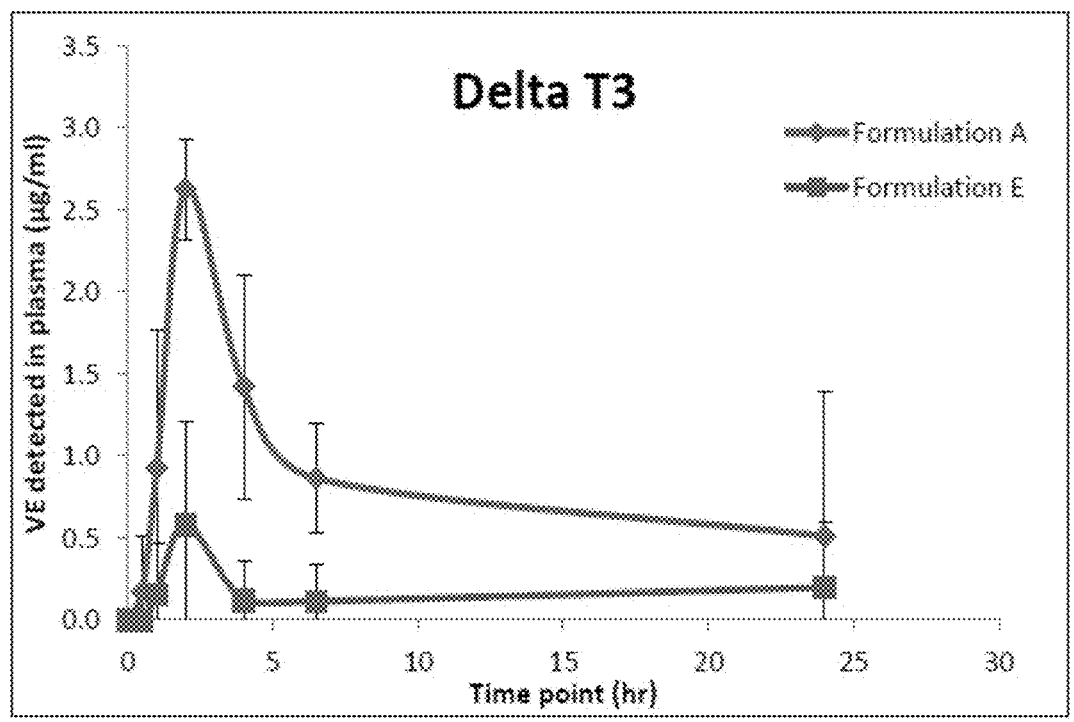

Three different oil carriers were then compared concerning the influence of the different oils on the absorption of vitamin E. In this study, a group of rats were administered orally with Formulation A and another group of rats were administered with Formulation C or D at 300 mg vitamin E per kg rat body weight. The difference between the formulations is the oil carrier used in Formulation A is GTO and the oil carrier used in Formulation C is olive oil while that in Formulation D is soybean oil. Blood samples were withdrawn from the rats at 0.5 hr, 1 hr, 2 hr, 4 hr, 6.5 hr and 24 hr, post-administration. Plasma was extracted from blood samples and analysed. The total VE detected in blood plasma versus time profiles of Formulations A and C is shown in FIG. 2 while that of Formulation A and D is shown in FIG. 3. The data shows that the total VE detected in the plasma from blood samples of the group of rats administered with Formulation A with the oil carrier of GTO was higher than both Formulations C and D. Therefore, the oil carrier plays an important role in enhancing vitamin E absorption in-vivo. The Area Under the Curve (AUC) of Formulation A is about 1.6 times that of Formulation C and D.

An additional formulation was prepared for comparison with Formulation A, namely the commercially available soft-gelatin capsules described as Formulation E (U.S. Pat. No. 6,596,306). Formulation E is a formulation that supposedly delivers fat-soluble drugs (including tocopherols, tocotrienols, vitamin A, D and β-carotene) in a SEDDS that offer superior oral absorption in-vivo. FIGS. 4a to 4d show the breakdown of the different VE isomers of alpha-tocopherol, alpha-tocotrienol, gamma-tocotrienol and delta-tocotrienols respectively for Formulation A and E. The data shows that Formulation A delivered much higher levels of tocotrienol isomers (alpha, gamma and delta) in the blood plasma compared to Formulation E. The difference ranges from about 3 times (gamma-tocotrienol) to about 5 times (delta-tocotrienol) higher absorption when comparing the two formulations. Overall, it is clear that Formulation A delivers much higher levels of tocotrienol isomers while Formulation E delivers slightly higher levels of alpha-tocopherol.

The formulation can be made into powder form, tablet or filled into a capsule or a gelatin capsule, including soft-shelled and hard-shelled capsules, food and beverages, emulsion systems, etc. The formulation is preferably to be administered orally. However, the formulation also can be in the other form for topical, parenteral, rectal, intrathecal, intra-peritoneal or intravenous infusion.

The preferred source for tocotrienols is either cereals such as rice, barley, oats, wheat and rye, and vegetable oils such as palm oil and rice bran oil.

While the disclosed formulation has been particularly shown and described with respect to the preferred embodiments, it is understood by those skilled in the art that various modifications in form and detail may be made therein without departing from the scope of the invention. Accordingly, this invention includes all modifications and equivalents of the subject matter recited in the claims appended hereto. Moreover, any combination of the above-described elements in all possible variations thereof is encompassed by the invention unless otherwise indicated herein or otherwise clearly contradicted by context.

The invention claimed is:

1. A method of delivering a tocotrienol to a subject in need of supplementing an intake of a daily allowance of a fat-soluble nutrient, the method comprising administering to the subject a dietary supplement comprising a self-emulsifying formulation comprising a fat-soluble compound selected from tocotrienols and derivatives thereof, wherein the amount of the fat-soluble compound is about 10% to about 50%, by weight of the formulation; two emulsifiers each selected from the group consisting of nonionic surfactants, wherein the emulsifiers are sorbitan monolaurate and polyoxyethylene sorbitan 20 monooleate (Polysorbate 80), wherein the amount of emulsifiers is about 15% to about 45%, by weight of the formulation, wherein the weight ratio of said sorbitan monolaurate to Polysorbate 80 is about 1:1 to about 1:20; and an oil carrier selected from the group consisting of glycerides, wherein the amount of oil carrier is about 6% to about 56%, by weight of the formulation.

2. The method as claimed in claim 1, wherein the weight ratio of said sorbitan monolaurate to Polysorbate 80 is about 1:2 to about 1:8.

3. The method as claimed in claim 1, wherein the fat-soluble compound is tocotrienol.

4. The method as claimed in claim 1, wherein the oil carrier is comprises glycerol trioleate (GTO) oil.

5. The method as claimed in claim 4, wherein said glycerol trioleate (GTO) oil includes the main triglycerides (TG) oftriolein (OOO, C18:1).

6. The method as claimed in claim 5, wherein said oil carrier comprises of the amount of triolein (OOO, C18:1) about 55% to about 99% by weight of said GTO oil.

7. The method as claimed in claim 5, wherein said oil carrier comprises of the amount of triolein (OOO, C18:1) about 65% to about 85% by weight of said GTO oil.

8. The method as claimed in claim 1 further comprising fatty acid selected from the group consisting of oleic acid, palmitic acid, stearic acid and mixtures thereof.

9. The method as claimed in claim 1, wherein the formulation is made into powder form, tablet or filled into a gelatin capsule.

10. The method as claimed in claim 9, wherein said formulation is filled into a gelatin capsule, in which said gelatin capsule is a hard-shelled gelatin capsule or a soft-shelled gelatin capsule.

11. The method as claimed in claim 1, wherein the formulation is in a form for oral delivery.

12. The method as claimed in claim 1, wherein the step of administering is performed orally.

13. The method as claimed in claim 1, wherein the step of administering is performed parenterally, rectally or topically.

* * * * *